(12) United States Patent
Maeda et al.

(10) Patent No.: US 7,592,137 B2
(45) Date of Patent: Sep. 22, 2009

(54) GENETIC TESTING KITS AND A METHOD OF BLADDER CANCER

(75) Inventors: Koshi Maeda, Hitachinaka (JP); Shinichi Fukuzono, Hitachinaka (JP); Takayuki Kanda, Hitachinaka (JP); Kokichi Sugano, Urayasu (JP)

(73) Assignees: Hitachi High-Technologies Corporation, Tokyo (JP); Tochigi Prefectural Office, Utsunomiya-shi, Tochigi (JP)

( * ) Notice: Subject to any disclaimer, the term of this patent is extended or adjusted under 35 U.S.C. 154(b) by 145 days.

(21) Appl. No.: 10/854,327

(22) Filed: May 27, 2004

(65) Prior Publication Data

US 2005/0009072 A1 Jan. 13, 2005

(30) Foreign Application Priority Data

May 28, 2003 (JP) .............................. 2003-151397

(51) Int. Cl.
*C07H 21/04* (2006.01)
*C12Q 1/68* (2006.01)

(52) U.S. Cl. ...................... 435/6; 435/91.1; 435/91.2; 536/23.1; 536/24.3

(58) Field of Classification Search ........................ None
See application file for complete search history.

(56) References Cited

U.S. PATENT DOCUMENTS

2003/0092019 A1* 5/2003 Meyer et al. .................... 435/6

FOREIGN PATENT DOCUMENTS

JP          H11-341999          12/1999

OTHER PUBLICATIONS

Orlow, Int. J. Cancer, vol. 75, pp. 819-824, 1998.*
Chihara et al. (Lab. Invest. vol. 85, pp. 895-907, 2005).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
"Single-Tube Multiplex PCR-SSCP Analysis Distinguishes 7 Common ABO Alleles and Readily Identifies New Alleles," by Shea Ping Yip, Blood, vol. 95, No. 4, Feb. 15, 2000, pp. 1487-1492.
"Genotypic and Phenotypic Characterization of the Histoblood Group ABO(H) in Primary Bladder Tumors," by Irene Orlow et al., Int. J. Cancer, vol. 75, No. 6, Mar. 16, 1998, pp. 819-824.
"Molecular Alterations in Bladder Cancer," by Torben F. Ørntoft et al., Urological Research, Springer Verlag, Berlin, DE, vol. 26, No. 4, Aug. 1998, pp. 223-233.
"Loss of Blood Group A Antigen Expression in Bladder Cancer Caused by Allelic Loss and/or Methylation of the ABO Gene," by Yoshitomo Chihara et al., Laboratory Investigation, vol. 85, No. 7, Jul. 2005, pp. 895-907.
Ogasawara, et al., "Extensive Polymorphism of ABO Blood Group Gene: Three Major Lineages of the Alleles for the Common ABO Phenotypes" Hum. Genet., vol. 97, pp. 777-783, 1996.
M. Shigyo, et al.; 2001; "Molecular Followup of Newly Diagnosed Bladder Cancer Using Urine Samples"; the Journal of Urology, vol. 166, pp. 1280-1285.
K. Sugano et al.; Dec. 2006; "Genetic alterations in bladder cancer and their clinical applications in molecular tumor staging"; Nature Clincal Practice Urology, vol. 3, No. 12, pp. 642-652.
C.H. Spruck et al.; 1994; "Two molecular pathways to transitional cell carcinoma of the bladder"; Cancer Res. vol. 54, pp. 784-788.
H. Matsuyama et al.; 1994; "Nonrandom numerical aberrations of chromosomes 7, 9, and 10 in DNA-diploid bladder cancer"; Cancer Genet. Cytogenet. vol. 77, pp. 118-124.
G. Dalbagni et al.; 1993; "Genetic alterations in bladder cancer"; Lancet vol. 342, pp. 469- 471.
M.A. Knowles et al.; 1994; "Allelotype of human bladder cancer"; Cancer Res. vol. 54, pp. 531-538.
A.F. Olumi et al.; 1990; "Allelic loss of chromosome 17p distinguishes high grade from low grade transitional cell carcinomas of the bladder"; Cancer Res. vol. 50, pp. 7081-7083.

* cited by examiner

*Primary Examiner*—Jeanine A Goldberg
(74) *Attorney, Agent, or Firm*—Dickstein Shapiro LLP (57) ABSTRACT

A deletion in the end region of the long arm of a Chromosome 9 is efficiently detected.

A genetic testing kit of bladder cancer according to the present invention includes a primer allowing for efficient amplification of a region containing a site of genetic polymorphism present in the ABO blood group gene of Chromosome 9. In the site of genetic polymorphism present in the ABO blood group gene, the frequency of heterozygote (heterozygosity) in the population is extremely high. Therefore, by detecting LOH using a polymorphic site present in the ABO blood group gene, it is possible to reliably detect a deletion near the polymorphic site, in other words, a deletion near the end of the long arm of Chromosome 9.

7 Claims, 4 Drawing Sheets

FIG. 1

SEQUENCE OF EXON 6 IN ABO BLOOD GROUP GENES GROUPS

TAGGAAGGATGTCCTCGTG
GTGACCCCCTTGGCTGGCTC
CCATTGTCTGGGAGGGCAC
GTTCAACATCGACATCCTC
AACGAGCAGTTCAGGCTCC
AGAACACCATTGGGTT
AACTGTGTTTGCCCATCAAG
AA

261st: SINGLE NUCLEOTIDE POLYMORPHIC SITE (ΔG)

297th: SINGLE NUCLEOTIDE POLYMORPHIC SITE (G/A)

GENETIC TESTING KITS AND A METHOD OF BLADDER CANCER

BACKGROUND OF THE INVENTION

1. Field of the Invention

The present invention relates to a genetic test for bladder cancer by analyzing a chromosome.

2. Background Art

It has been reported that when canceration of the bladder cells occurs, a loss in a chromosome takes place, and consequently loss of heterozygosity (LOH) frequently occurs at 4p, 8p, 9p, 9q, 11p and 17p sites (see nonpatent documents 1 to 5). Therefore, bladder cancer can be effectively tested by detecting LOH. However, this method uses the tissue cells excised from bladder cancer, and therefore, a more simplified method has been strongly desired.

The patent document 1 discloses a method of testing bladder cancer by analyzing LOH of Chromosome 9 using nucleic acids recovered from the urine of an early-stage bladder cancer patients. In this test method, a deletion in chromosome 9 is detected by using a single nucleotide polymorphism (SNP) and a microsatellite type polymorphic site which differs in number of repeat units by one or more, in the short arm (9p) and the long arm (9q) of Chromosome 9. More specifically, after the region having a genetic polymorphism on Chromosome 9 is amplified by PCR, the resultant PCR product is blunted, and the obtained nucleic acid fragment is analyzed by a single-strand conformation polymorphism (SSCP) to detect LOH at a site of genetic polymorphism.

Nonpatent document 1
Cancer Res. 54, p 784-788, Spruck III et al. (1994)
Nonpatent document 2
Cancer Genet. Cytogenet., 77 p 118-124, Matsuya et al. (1994)
Nonpatent document 3
Lancet 342, p 469-471, Dalbagni et al. (1993)
Nonpatent document 4
Cancer Res. 54, p 531-538, Knowles et al. (1994)
Nonpatent document 5
Cancer Res. 50, p 7081-7083, Olumi et al. (1990)
Patent document 1
JP Patent Publication (Kokai) No. 11-341999

In the test method of the patent document 1, since the frequency of occurrence of heterozygotes is low at a site of genetic polymorphism within the region of the VAV2 gene used near the end of the long arm (9q32 to q34.3), analysis of LOH cannot be performed in some cases. For this reason, in a conventional bladder cancer test, it is difficult to identify a deletion in a chromosome near the end of the long arm, which raises a problem that such a test cannot be performed efficiently.

Accordingly, the present invention is directed to efficiently identifying a deletion in a chromosome 9 near the end of the long arm.

SUMMARY OF THE INVENTION

We have conducted intensive studies and found that a deletion in the end region of the long arm of Chromosome 9 can be efficiently detected by using a site of genetic polymorphism present in the ABO blood group gene present in Chromosome 9 to accomplish the present invention.

A genetic testing kit of bladder cancer according to the present invention comprises a primer allowing for efficient amplification of a region containing a site of genetic polymorphism present in the ABO blood group gene of Chromosome 9. In the site of genetic polymorphism present in the ABO blood group gene, a heterozygote (heterozygosity) occurs at a high frequency in the population. Therefore, by using a polymorphic site present in the ABO blood group gene, a deletion near the polymorphic site, in other words, a deletion near the end region of the long arm of Chromosome 9 can be detected reliably.

Those and other novel features and advantages of the present invention will be now described with reference to the accompanying drawings.

DESCRIPTION OF SYMBOLS 1 test device, 2 nucleic acid extracting section, 3 nucleic acid mixing section, 4 nucleic acid amplification section, 5 detecting section.

DETAILED DESCRIPTION OF THE PREFERRED EMBODIMENTS

A method of testing for bladder cancer using the present invention comprises the steps of:

a) analyzing sites of genetic polymorphism of Chromosome 9 including a site of genetic polymorphism present in the ABO blood type gene; and b) detecting loss of heterozygosity based on the results of the analysis for the sites of genetic polymorphism.

In a method of testing for bladder cancer according to the present invention, the bladder cancer includes early-stage cancer of Grade 1 or lower according to the WHO-grade classification partially amended, and superficial bladder cancer such as pTa, pT1 or pTis according to the TNM classification (tumor-nodes-metastasis pathological staging system: American Joint Committee on Cancer (1988)).

Step a

Figure 1:
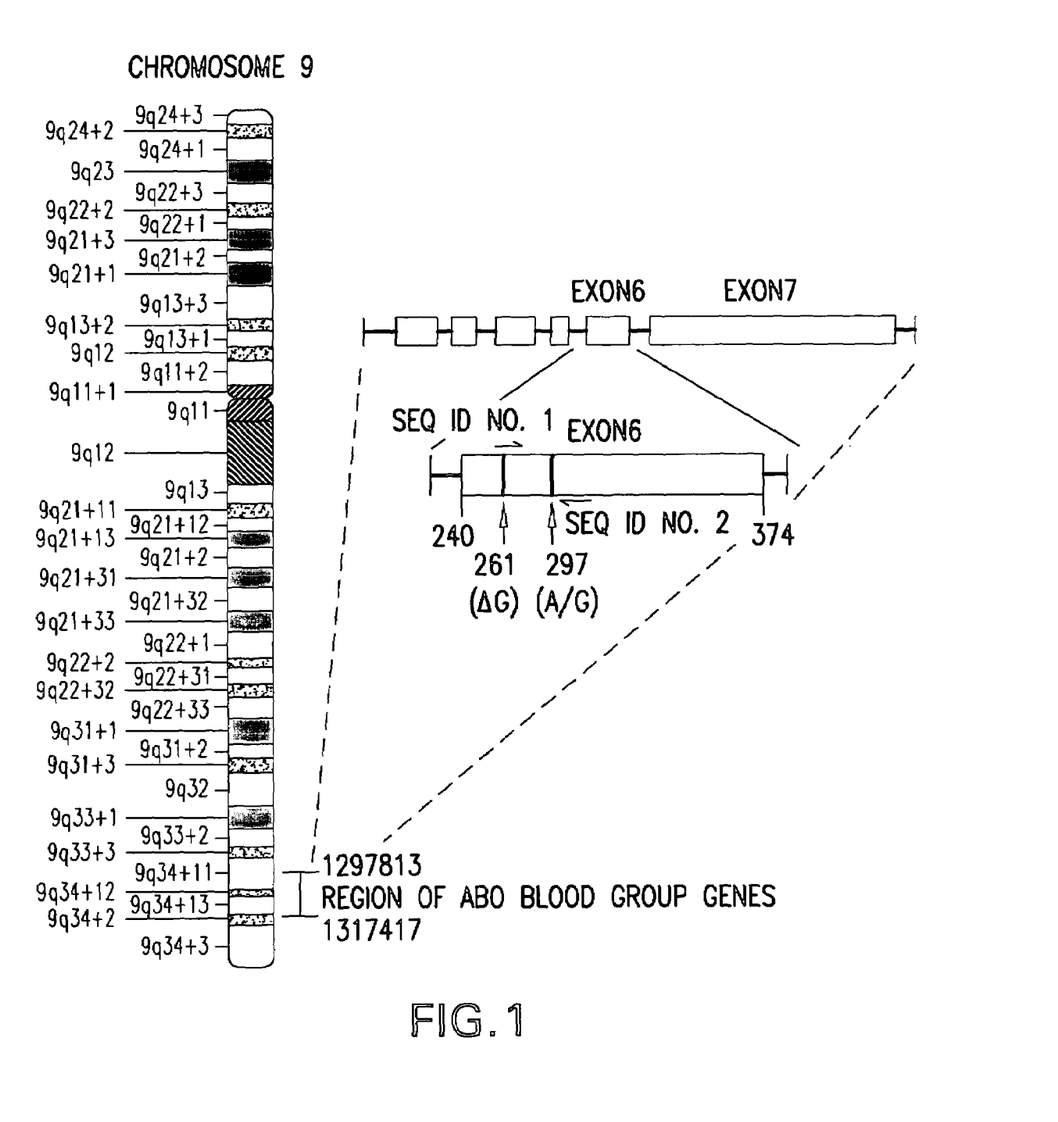
FIG. 1 shows an enlarged illustration of Chromosome 9 and ABO blood group gene of the Chromosome 9.

The "site of genetic polymorphism present in the ABO blood group gene" used herein means that present in the range of 9q34.1 site to 9q34.2 site of Chromosome 9, as shown in FIG. 1. Specifically, the site of genetic polymorphism used herein means that present within Exon 6 of the ABO blood group gene. More specifically, it refers to the 261st base and/or the 297th base from the initiating codon of cDNA (SEQ ID NO:4), which has been designated under registration number AF134412 at the GenBank. The genotype of the 261st site of genetic polymorphism used herein is guanine or deletion of guanine, whereas the genotype of the 297th site of genetic polymorphism is guanine or adenine. Note that the polymorphic site present in the ABO blood group gene is not limited to these. For example, the site of genetic polymorphism disclosed in Hum Genet (1996) 97: 777-783 may be used.

The "sites of genetic polymorphism" used herein include at least those present in the ABO blood group gene. The sites of genetic polymorphism may include a site of genetic polymorphism present in the ABO blood group gene and other sites of genetic polymorphism present in Chromosome 9. The other sites of genetic polymorphism used herein include, but not particularly limited to, D9S304, D9S303, ALDOB, D9S775, and VAV2 disclosed in JP Patent Publication (Kokai) No. 11-341999. The "ALDOB" refers to a genetic polymorphic site with a single nucleotide replaced in Intron 8 of a human aldorase B (ALDOB) gene on Chromosome 9 and has been identified to be present on 9q22 (Am. J. Hum. Genet. 52 p 835-840, Brooks et al. (1993)). The VAV2 is a site of genetic polymorphism on VAV2 gene produced by T/C replacement and identified to be present on 9q34. This was found in the National Cancer Center hospital based on the determination data of the base sequence of a cosmid clone L196C8 strain (GenBank accession No. AC002111). Further, D9S304, D9S303, and D9S775 are microsatellite type polymorphism, which are 4-base unit repeats, and available from "the GDB Human Genome Database" at the GDB website.

The analysis used in the step a means the one which can detect loss of heterozygosity in the following step b based on its results. More specifically, the analysis in the step a, so-called nucleic acid amplification is carried out such that a region containing individual sites of genetic polymorphism (including sites of genetic polymorphism present on the ABO blood type gene) constituting the sites of genetic polymorphism is amplified. Thereafter, whether a nucleic acid fragment was amplified or not is checked.

In the method for testing bladder cancer according to the present invention, a sample to be tested may be prepared immediately before the step a. Alternatively, a sample prepared in advance may be tested. Examples of such a sample may include a biological sample such as urine. The biological sample used herein may include tumor tissues themselves. The tumor tissues may be taken by a surgical operation or biopsy.

Example of urine sample include, but not limited to, those taken at the time of group examination, medical checkup, complete physical examination, and checkup by mail; and urine taken from inpatients and outpatients, for use in early detection of bladder cancer in order to find occurrence and recurrence of bladder cancer. In addition, cells falling in urine and collected efficiently by a specific urine-collecting device with a designed urine collecting method.

In amplifying a nucleic acid in the step a, the nucleic acid is extracted from a collected sample. A method of extracting a nucleic acid is not particularly limited and any conventionally known method may be used. For example, a nucleic acid may be extracted from cells present in urine or cells taken from the tissues of a subject to be tested. When urine is collected from a subject to be tested, any cells falling in the urine may be used as long as they contain a nucleic acid of the subject. Usually, a nucleic acid derived from normal cells and/or cancer cells falling in the urine by metabolism can be efficiently extracted by various methods.

Examples of the nucleic acid amplification method performed in the step a include, but not particularly limited, a polymerase chain reaction (PCR) method, strand displacement amplification (SDA) method, isothermal and chimeric primer-initiated amplification of nucleic acids (ICAN) method, and Loop-mediated isothermal amplification (LAMP) method. Any of the methods mentioned above may be performed using a genetic testing kit of bladder cancer containing a primer allowing for amplification of a region containing a site of genetic polymorphism present in the ABO blood group gene. The primer contained in the genetic testing kit of bladder cancer may have any base sequence as long as it allows for amplification of the region containing "the site of genetic polymorphism present in the ABO blood group gene" mentioned above.

Figure 2:
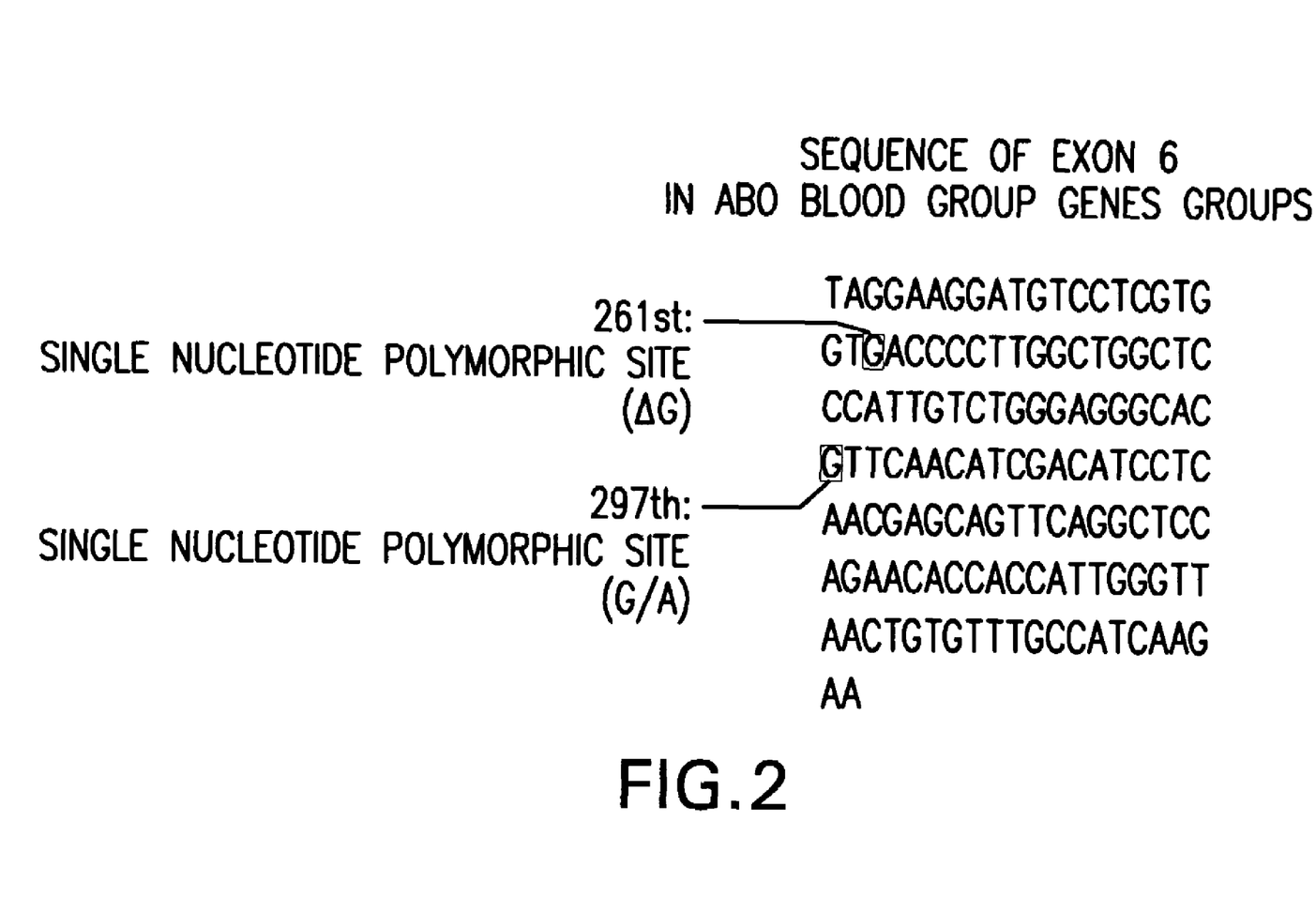
FIG. 2 shows the gene sequence (SEQ ID NO:3) of Exon 6 of the ABO blood group gene.

Examples of such a primer may include a pair of primers constituted of a first primer, which has 5 or more continuous bases of a base sequence represented by SEQ ID NO:1, and a second primer, which has 5 or more continuous bases of a base sequence represented by SEQ ID NO:2. Specifically, the first primer may be the base sequence represented by SEQ ID NO:1, that is, 5'-TCTCCATGTGCAGTAGGAAAGGATG-3'; and the second primer may be the base sequence represented by SEQ ID NO:2, that is, 5'-CACAGTTAAC-CCAATGGTGGTGTT-3'. In addition, as the primer, a primer designed so as to amplify a partial sequence of Exon 6 of the gene shown in FIG. 2, may be used.

In amplifying a region containing a site of genetic polymorphism except those sites present in the ABO blood group gene of Chromosome 9, a primer may be designed based on the base sequence information of the region. In amplifying each of regions containing the other sites of genetic polymorphism, such as D9S304, D9S303, ALDOB, D9S775 or VAV2, a base sequence near a target site of polymorphism is obtained based on the aforementioned data base and then a primer can be designed based on the base sequence thus obtained.

Furthermore, these primers may be designed so as to amplify a region of 100 to 200 bp in length. In order to facilitate the detection of a nucleic acid fragment performed in the step b (described later), a primer may be labeled. A nucleic acid fragment may be labeled during PCR by using bases labeled with radioactive phosphorus or may be labeled after PCR is completed. A labeling method is not particularly limited as long as a label is easily detected after the step b (described later). Examples of such a labeling method include those using radioactive substances, fluorescent substances, chemiluminescence substances, and biotin (detectable by enzyme labeled avidin). As to a primer, it may be fluorescently labeled in advance with an A.L.F.red (Cy5™) amidite (manufactured by Pharmacia) at an end. Examples of applicable fluorescent labels include FAM™, TET™, HEX™, TAMRA™, and ROX™ manufactured by Applied Biosystems. In these cases, either the 5' end or the 3' end of a primer may be labeled, and preferably, the 5' end of a primer may be labeled.

In the step a, after a nucleic acid is amplified by using the biological sample to be tested and the primer as mentioned above, whether a nucleic acid fragment is amplified or not is checked. The presence or absence of an amplified nucleic fragment is checked by subjecting a reaction solution to electrophoresis for single-strand conformation polymorphism (SSCP) analysis. More specifically, after the nucleic acid amplification reaction, the nucleic acid fragment is blunted and can be subjected to a capillary electrophoresis apparatus. Since a nucleic acid fragment is labeled as mentioned above, whether the nucleic acid fragment is amplified or not can be checked by using the label as an indicator.

Note that in the step a, any method may be used such that loss of heterozygosity can be detected, that is, genetic polymorphism analysis can be made in the step b. A method of analyzing genetic polymorphism is not limited to the aforementioned method in which a nucleic acid is amplified followed by using capillary electrophoresis. Examples of a method of providing the results based on which loss of heterozygosity can be detected in the step b, include a method using a mass spectroscope, RT-PCR method, and branched nucleic acid hybridization method (b-nucleic acid). Besides these, a method of detecting LOH using ATP converted from a by-product formed during an elongation reaction, and a nucleic acid microarray may be used. Actually, in the genetic polymorphism analysis mentioned above, it is desirable to use a method capable of quantitatively determining genetic polymorphism.

When a mass spectroscope is used, a primer is designed so as to allow for amplification of nucleic acid fragments having a length varied with the pattern of a site of genetic polymorphism, and this primer is applied to nucleic acid amplification. Thereafter, the mass of the amplified nucleic acid fragments different in base length is determined by a mass spectroscope, thereby checking the presence or absence of a nucleic acid fragment.

In the step a, a primer is designed such that an elongation reaction of a nucleic acid amplification method proceeds depending upon difference in pattern at a site of genetic polymorphism. In a system where light emission is induced by a by-product (ATP) produced when the elongation reaction takes place, light emission is measured by a general-purpose luminescence determination device.

In the step a, a nucleic acid microarray may be used. This assay uses two sets of primers having the same base sequence but labeled with fluorescence labels different in wavelength. To amplify the nucleic acid derived from a normal cell is performed using one set of the primers, whereas to amplify the nucleic acid derived from a cancer cell is performed using the other set. The amplified nucleic acid fragments derived from the normal cell and the cancer cell are mixed and fluorescence is detected by a nucleic acid microarray.

Step b

After the step a, loss of heterozygosity is detected in the step b based on the analysis results for sites for genetic polymorphism performed in the step a. The term of "loss of heterozygosity (LOH)" used herein refers to disappearing of one of the alleles of a heterozygote (which has different alleles from a father and a mother) present in a site of genetic polymorphism. Therefore, in the step b, the heterozygosity in Chromosome 9 of a subject to be tested is detected based on the analysis results in the step a, thereby detecting at least one of deletions in either one of Chromosomes 9 (in other words, from a farther and/or a mother). The phrase "at least one of deletions in either one Chromosomes 9" includes a case where one of Chromosomes 9, (homologous chromosomes) completely or partially disappears, and a case where mutually different gene sites of homologous chromosomes.

In the step a, when a nucleic acid amplifying method is performed and subsequently a capillary electrophoresis method is performed, the presence or absence of a nucleic acid fragment can be checked by the electrophoresis method. Therefore, loss of heterozygosity in Chromosome 9 can be detected. More specifically, this is a method for detecting LOH by analyzing a nucleic acid fragment by a single-strand conformation polymorphism (SSCP) analysis. Particularly, as a method of detecting LOH by amplifying a nucleic acid fragment by PCR using Taq polymerase, blunt-ending the end of the PCR product, and analyzing the resultant nucleic acid fragment by SSCP, a method disclosed by JP Patent Publication (Kokai) No. 9-201199 may be used.

Figure 3:
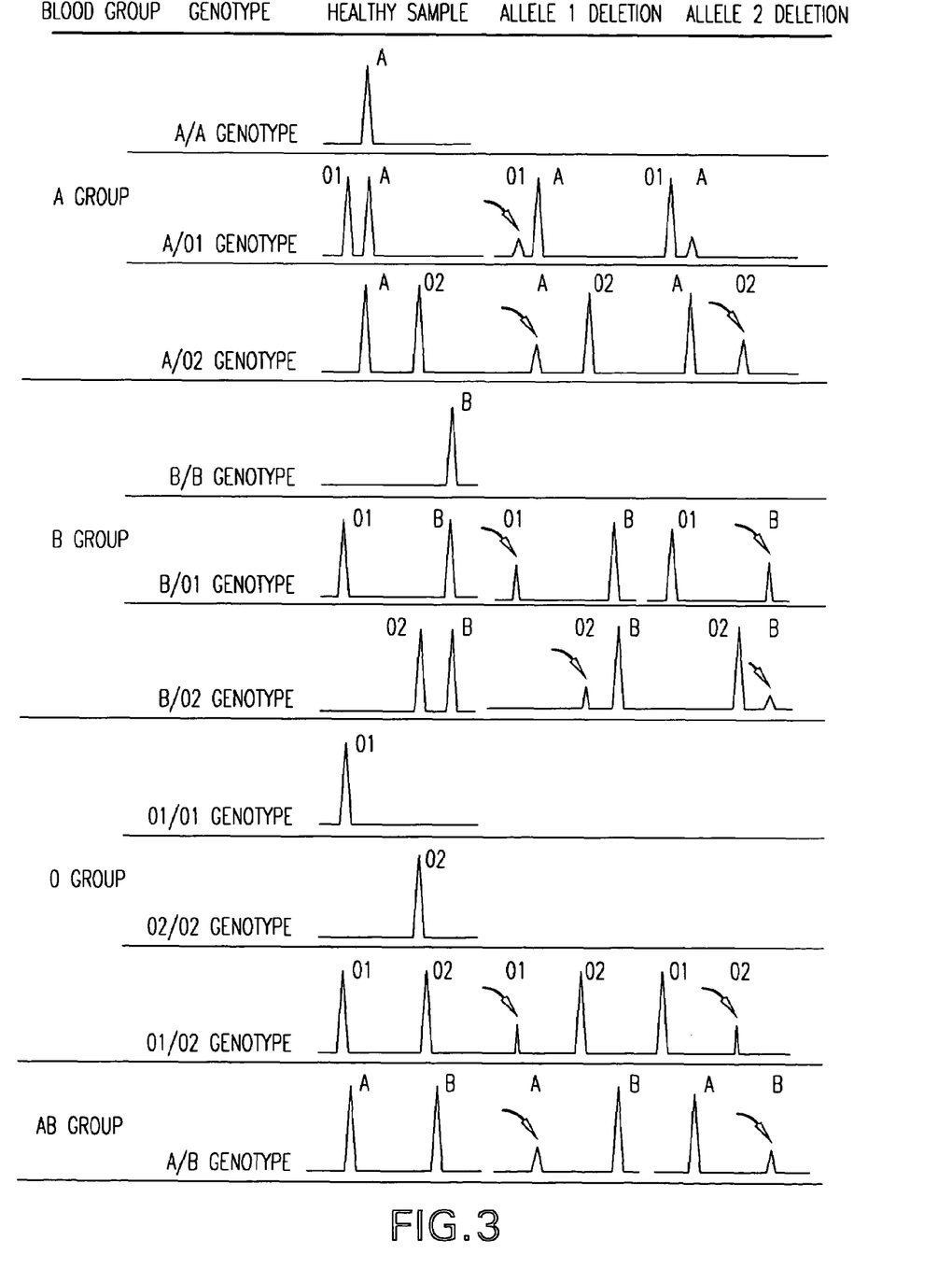
FIG. 3 shows the results of SSCP analysis.

The results of SCCP can be shown as peaks which vary in every allele depending upon the pattern of a site of genetic polymorphism contained in a nucleic acid fragment, as shown, for example, in FIG. 3. Each blood type shown in FIG. 3 has a plurality of genotypes which are determined by combination of two sites of genetic polymorphism. More specifically, in the genotype of A group (formally called "A101" group), the 261st polymorphic site is guanine, whereas the polymorphic site of the 297th site is adenine. In the genotype of B group (formally called "B101" group), the 261st polymorphic site is guanine and 297th polymorphic site is guanine. Similarly, in the genotype of O1 group (O101 group), the guanine of the 261st is deleted and adenine is present at the 297th site, whereas in the genotype of O2 group (O201 group), guanine of the 261st is deleted and guanine is present at the 297th site. The genotype determining a human blood group is determined by the genotypes of alleles derived from parents. When these four genotypes are combined, a total of ten genotypes are produced as shown in FIG. 3. Actually, since a deletion in chromosomes 9 is not always present in all test samples, the peak does not completely disappear but decreases in height as shown in FIG. 3. As is apparent from FIG. 3, when a predetermined region of Chromosome 9 is deleted, the peak corresponding to the deleted region becomes lower than that of a sample derived from a healthy person. Accordingly, the presence or absence of a nucleic acid fragment is determined by detecting peaks which are different for each of the 10 genotypes, thereby specifying the deletion in chromosome 9 of a subject to be tested.

In the step a, when nucleic acids are amplified and subsequently the nucleic acid fragments are analyzed for genetic polymorphism by a mass spectroscope, the nucleic acid fragments having different masses can be detected by the mass spectroscope. From the detection results, the presence or absence of a nucleic acid fragment is obtained and further, based on this, loss of heterozygosity in Chromosome 9 can be detected.

In particular, in the method of testing a bladder cancer according to the present invention, LOH is detected using a site of genetic polymorphism present in the ABO group blood gene. In the site of genetic polymorphism present in the ABO group blood gene, the frequency of a heterozygote (heterozygosity) in the population is extremely high. Therefore, it is possible to reliably detect a deletion near the site of genetic polymorphism in Chromosome 9. In other words, by detecting LOH using a site of genetic polymorphism present in the ABO blood group gene, a deletion near the end of the long arm of Chromosome 9 can be detected reliably.

When the 261st and 297th sites of genetic polymorphism of Exon 6 of the ABO blood group gene are used as the site of genetic polymorphism present in the gene, either one of these two sites of genetic polymorphism may be a heterozygote. Therefore, the deletion near the site of genetic polymorphism in Chromosome 9 (near the end of the long arm of Chromosome 9) can be reliably detected.

In addition to a site of genetic polymorphism present in the ABO blood group gene, a site of genetic polymorphism except those sites in the ABO blood group gene is used to detect the deletion near sites of genetic polymorphism of all these genes. More specifically, by appropriately selecting sites of genetic polymorphism to be analyzed in the step a from those present in Chromosome 9 so as to cover the entire Chromosome 9, deletions can be detected over the entire Chromosome 9. For example, by detecting LOH with respect to D9S304, D9S303, ALDOB, and D9S775 in addition to the site of genetic polymorphism present in the ABO blood group gene, deletions can be detected in the entire chromosome 9. As described above, by detecting deletions over the entire Chromosome 9, the malignancy of bladder cancer can be checked.

Figure 4:
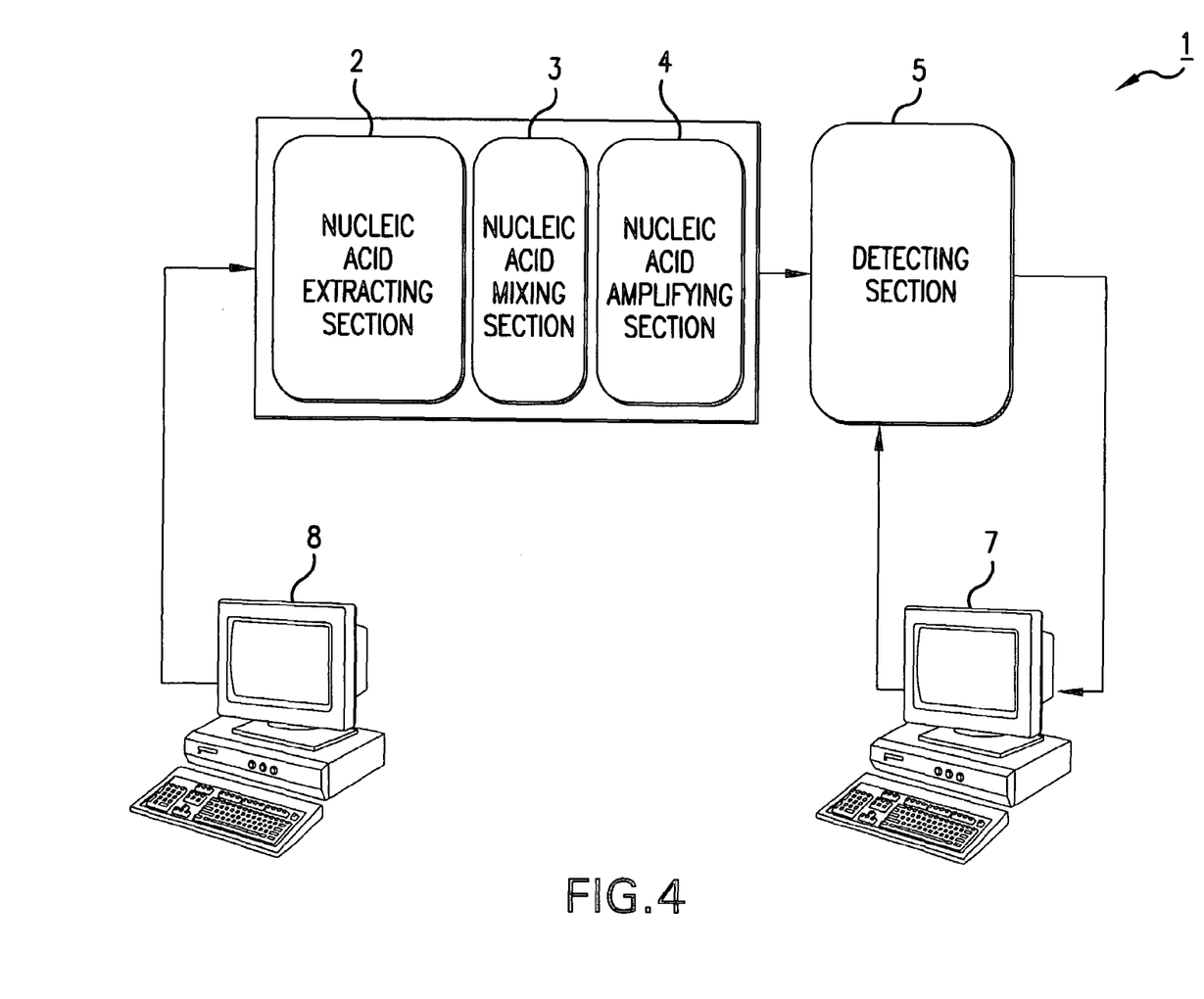
FIG. 4 shows a schematic view of a test device for testing for bladder cancer.

The steps a and b mentioned above may be carried out by a test device 1, for example, shown in FIG. 4. The test device 1 comprises a nucleic acid extracting section 2, which extracts a nucleic acid from a biological sample, a nucleic acid mixing section 3, which mixes the nucleic acid extracted and the reaction solution contained in the testing kit of bladder cancer, and a nucleic acid amplifying section 4, which amplifies the nucleic acid using a nucleic acid contained in the reaction solution as a template. The test device 1 further comprises a detecting section 5, which detects a nucleic acid fragment contained in the reaction solution. Furthermore, the test device 1 comprises an operation/output section 7, which inputs operational conditions regarding the nucleic acid extracting section 2, nucleic acid mixing section 3, and nucleic acid amplification section 4 and receives data output from these sections. Moreover, the test device 1 comprises an operation/LOH analyzing section 8, which inputs operational conditions to the detecting section and received detection data output from the detecting section.

Using the test device 1 thus constituted, extraction of a nucleic acid from a biological sample taken from a subject to be tested, preparation of a reaction solution, the amplification reaction of a nucleic acid contained in the reaction solution, and detection of LOH can be automatically performed. Furthermore, analysis of many test objects can be simultaneously performed using the test device 1.

EXAMPLES

The present invention will now be described by way of Experimental Examples and Examples, which should not be construed as limiting the technical field of the present invention.

Experimental Example 1

1. Obtaining Sample

Samples of bladder cancer patients were obtained as described below, treated, and stored until LOH analysis. Part of fresh tissues obtained by transuretheral resection (TUR) or biopsy was placed in a 1.5 mL Eppendorf tube and stored in a frozen state at −80° C. Urine was collected in a 50 mL centrifuging tube by natural excretion before endoscopy. After the collected urine was centrifuged at 1,000 rpm for 5 minutes, the supernatant was discarded and the pellet was collected. To the pellet, 40 mL of a physiological salt was added to re-dispersed and centrifuged again at 1,000 rpm for 5 minutes. After the supernatant was discarded and the remaining pellet was stored in a frozen state at −80° C. The nucleic acid from normal tissues was extracted from peripheral blood leukocytes (PBL). More specifically, 10 mL of venous blood was collected in a blood collecting tube containing heparin. After the tube was centrifuged at 3,000 rpm for 15 minutes, the blood plasma was discarded. To the blood collecting tube, 40 mL of 0.2% physiological saline was added to cause hemolysis and centrifuged again at 3,000 rpm for 15 minutes. After the supernatant was discarded, the same procedure was repeated twice. The remaining pellet was stored in a frozen state at −80° C. Negative control samples were prepared by taking urine and blood from 20 patients of nonmalignant urinary tract disorder and treating them in the same manner as in bladder cancer patients. The obtained negative control samples were stored in a frozen state at −80° C.

2. Extraction of Nucleic Acid

A nucleic acid was extracted from a freeze-stored sample obtained in step 1 by digesting the sample with Proteinase K and extracted with phenol/chloroform in accordance with a method disclosed by Davis et al. (Basic Method in Molecular Biology, published by Elsevir Science Publishing) or Sugano et al. (Lab. Invest. 68 p 361-366 Sugano et al. (1993)). In brief, to the sample treated at 65° C. for 15 minutes, a 10 mmol/L Tris-hydrochloric acid buffer containing 1 mg/mL protease K, 10 mmol/L EDTA, 0.4% sodium dodecyl sulfate (SDS), 150 mmol/L NaCl was added. After the reaction mixture was incubated at 37° C. overnight, an equivalent amount of solution containing phenol and chloroform in a ratio of 1:1 was added thereto, nucleic acid was extracted twice. To the extraction solution, 0.1V of a 3 mol/L sodium acetate solution and 2.5V of cold anhydrous ethanol were added. The solution mixture was cooled at −20° C. for 2 hours to precipitate the nucleic acid. To urine and cancer tissue samples, 20 μg of glycogen serving as a carrier for ethanol precipitation was added to improve the recovery of nucleic acid. The solution was centrifuged to collect a precipitate. Further, 1 mL of 80% ethanol was added to the precipitate to wash it and thereafter dried and solidified in a vacuum centrifugation concentration machine. The precipitate containing a nucleic acid was re-dissolved with a TE buffer.

3. Preparation of Fluorescent Labeled Oligonucleotide Primer

The primers for amplifying a region containing a site of genetic polymorphism present in the ABO group blood gene on Chromosome 9 are summarized in Table 1.

TABLE 1

| Primer Sequence | |
|---|---|
| SEQ ID No. 1 | 5'-Cy5TCTCCATGTGCAGTAGGAAAGGATG-3' |
| SEQ ID No. 2 | 5'-CACAGTTAACCCAATGGTGGTGTT-3' |

Using A.L.F.red™ (Cy5™) amidite reagent (Pharmacia), a PCR primer represented by SEQ ID No. 1 was labeled at the 5' terminal with indodicarbocyanine (Cy5). As a site of genetic polymorphism, the site (ABO Exon 6) of Exon 6 of the ABO blood group gene on Chromosome 9 was used. The ABO Exon 6 is identified as a range of 9q34.1 to 9q34.2 site. The primer sequences shown in Table 1 were specifically optimized by the present inventors so as to fit SSCP of genetic polymorphism useful for testing bladder cancer recurrence.

4. PCR

First, 0.1 μg of a genomic nucleic acid (template) extracted from a biological sample and primers shown in table 1 (1.0 pM per each) were added to 10 nM nucleotide triphosphate (dNTP), 10 μM tris hydrochloric acid buffer (pH 8.3), 50 mM KCl, 1.5 mM MgCl.sub.2, 0.001% (w/v) gelatin, and 1.25 units of Taq nucleic acid polymerase (manufactured by Perkin Elmer) to bring a total amount to 25 μl. The solution was subjected to PCR under the following conditions. PCR was performed by denaturing a reaction at 95° C. for 12 minutes and subsequently performing 35 cycles of 95° C. for 30 seconds, 57° C. for 30 seconds, 72° C. for 30 seconds, and thereafter performing an elongation reaction at 72° C. for 7 minutes.

5. Blunt-Ending of the 3' End of PCR Product

A nucleic acid fragment amplified by PCR was processed by Klenow fragment (manufactured by Takara Shuzo) and blunted. To 5 μL of the PCR product, 1 μl of a Klenow fragment (0.5 units) was added. After the mixture was reacted at 37° C. for 30 minutes, 1 μL of 100 mM EDTA was added (Genes. Chromosomes & Cancer 15, p 157-164, Sugano et al. (1996))

6. Single-Strand Conformation Polymorphism Analysis (SSCP Analysis)

The nucleic acid fragment blunt ended was analyzed by electrophoresis device, A.L.F.red™ (manufactured by Pharmacia) using polyacrylamide gel and a Tris/glycine buffer (Tris: 15% (w/v) and Glycine: 3.2% (w/v)) at a temperature of 18° C., 25 W, for 1,500 minutes.

Example 2

The Ratio of Heterozygotes Between VAV2 and ABO Exon 6

The ratio of heterozygotes between VAV2 and ABO Exon 6 was compared, both having a site of genetic polymorphism virtually at the same place (9q34) of chromosome 9 (Table 2). In VAV2 used as a site of genetic polymorphism of a conventional gene, heterozygote was found in 30 of 72 bladder cancer patients. The ratio of heterozygote was about 41.7%. In contrast, in ABO Exon 6, heterozygote was found in 57 of 72 bladder cancer patients. The ratio of heterozygote was about 79.2%.

TABLE 2

|  | Blood group | Total sample number | Heterozygote | Heterozygote (%) |
| --- | --- | --- | --- | --- |
| VAV2 | A | 25 | 11 | 44.0 |
|  | B | 15 | 7 | 46.7 |
|  | O | 20 | 7 | 35.0 |
|  | AB | 12 | 5 | 41.6 |
|  | Total | 72 | 30 | 41.7 |
| ABO Exon 6 | A | 25 | 20 | 80 |
|  | B | 15 | 15 | 100 |
|  | O | 20 | 10 | 50.0 |
|  | AB | 12 | 12 | 100 |
|  | Total | 72 | 57 | 79.2 |

From the results shown in Table 2, it becomes clear that a deletion near the end of the long arm of Chromosome 9 can be efficiently detected by detecting LOH using a site of genetic polymorphism present in the ABO blood type gene, thereby greatly improving the test performance for detecting bladder cancer.

According to the present invention, a deletion near the end of the long arm of chromosome can be efficiently identified.

What is claimed is:

1. A method for detecting loss of heterozygosity in human, comprising analyzing a biological sample of a human subject for a polymorphic genotype or genotypes at, at least, one of the 261st and the 297th sites of the sequence of SEQ ID NO:4 located in the ABO blood group gene on Chromosome 9, and detecting loss of heterozygosity at said site or sites based on the presence of heterozygosity of the results of the polymorphism analysis, wherein the polymorphic genotype at the 261st is guanine or deletion of guanine and the polymorphic genotype at the 297th site is guanine or adenine, and wherein the detection of the loss of heterozygosity is indicative of, at least, a partial deletion of Chromosome 9.

2. The method according to claim 1, wherein the analysis is performed by amplifying a nucleic acid region containing said site or sites of polymorphism.

3. The method according to claim 2, wherein the amplification is performed by using a first primer containing 5 or more continuous bases of the base sequence 5'-TCTCCAT- GTGCAGTAGGAAAGGATG-3' (SEQ ID NO:1) and a second primer containing 5 or more continuous bases of the base sequence 5'-CACAGTTAACCCAATGGTGGTGTT-3' (SEQ ID NO:2).

4. The method according to claim 1, wherein the loss of heterozygosity is detected by a single-strand conformation polymorphism analysis.

5. The method according to claim 4, wherein single-strand conformation polymorphism analysis is performed by capillary electrophoresis.

6. The method of claim 1 further comprising analyzing the biological sample for a polymorphic genotype or genotypes at, at least, one additional site selected from the group consisting of D9S304, D9S303, ALDOB, and D9S775, and detecting loss of heterozygosity at said site or sites based on the presence of heterozygosity of the results of the polymorphism analysis, wherein the loss of heterozygosity at any of said sites is indicative of, at least, a partial deletion of Chromosome 9.

7. The method of claim 6, wherein the analysis is performed by amplifying a nucleic acid region containing the site or sites of polymorphism.

* * * * *

UNITED STATES PATENT AND TRADEMARK OFFICE
CERTIFICATE OF CORRECTION

PATENT NO. : 7,592,137 B2
APPLICATION NO. : 10/854327
DATED : September 22, 2009
INVENTOR(S) : Maeda et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 240 days.

Signed and Sealed this

Twenty-first Day of September, 2010

David J. Kappos
*Director of the United States Patent and Trademark Office*

```
                        SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence:Synthezised
      DNA

<400> SEQUENCE: 1
tctccatgtg cagtaggaaa ggatg                                         25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:Synthezised
      DNA

<400> SEQUENCE: 2
cacagttaac ccaatggtgg tgtt                                          24
```